US006448279B1

(12) United States Patent
Tseng et al.

(10) Patent No.: US 6,448,279 B1
(45) Date of Patent: Sep. 10, 2002

(54) ISOTHIAZOLONE/AMINE OXIDE WOOD PRESERVATIVES

(75) Inventors: Chuen-Ing Tseng, Lawrenceville, NJ (US); Leigh Walker, Macungie, PA (US)

(73) Assignee: Lonza Inc., Fair Lawn, NJ (US)

( * ) Notice: Subject to any disclaimer, the term of this patent is extended or adjusted under 35 U.S.C. 154(b) by 0 days.

(21) Appl. No.: 09/578,048

(22) Filed: May 24, 2000

Related U.S. Application Data

(60) Provisional application No. 60/135,561, filed on May 24, 1999.

(51) Int. Cl.$^7$ ............................ A01N 43/80; A61K 31/425
(52) U.S. Cl. ..................................................... 514/372
(58) Field of Search ................................. 574/372

(56) References Cited

U.S. PATENT DOCUMENTS

| | | | |
|---|---|---|---|
| 3,296,145 A | 1/1967 | Findlan et al. ............... 252/106 |
| 3,484,523 A | 12/1969 | Findlan et al. ............... 424/248 |
| 3,761,488 A | 9/1973 | Lewis et al. ................. 260/302 |
| 4,005,193 A | 1/1977 | Green et al. ................. 424/168 |
| 4,105,431 A | 8/1978 | Lewis et al. .................... 71/67 |
| 4,379,810 A | 4/1983 | Amundsen et al. .......... 428/541 |
| 4,382,105 A | * 5/1983 | Amundsen et al. .......... 427/370 |
| 4,622,248 A | 11/1986 | Leach et al. ................. 427/440 |
| 4,857,322 A | 8/1989 | Goettsche et al. ........... 424/633 |
| 4,929,454 A | 5/1990 | Findlay et al. .............. 424/638 |
| 4,937,143 A | 6/1990 | West ........................ 427/419.8 |
| 4,950,685 A | 8/1990 | Ward ........................... 514/479 |
| 5,073,570 A | 12/1991 | Tseng ......................... 514/533 |
| 5,276,029 A | 1/1994 | Goettsche et al. ......... 514/231.2 |
| 5,304,237 A | 4/1994 | Barth et al. ................. 106/18.3 |
| 5,426,121 A | 6/1995 | Bell ............................ 514/500 |
| 5,468,284 A | 11/1995 | Sturm ............................ 106/2 |
| 5,486,315 A | 1/1996 | Tseng ......................... 252/547 |
| 5,527,384 A | 6/1996 | Williams et al. .......... 106/18.32 |
| 5,536,305 A | * 7/1996 | Yu ............................ 106/18.33 |
| 5,536,505 A | 7/1996 | Yu ............................ 106/18.33 |
| 5,833,741 A | 11/1998 | Walker ........................... 106/2 |
| 5,858,921 A | 1/1999 | Magin et al. ................ 504/206 |
| 5,922,672 A | 7/1999 | Stringer et al. ............. 510/503 |
| 6,180,672 B1 | 1/2001 | Lichtenberg et al. ........ 514/561 |

FOREIGN PATENT DOCUMENTS

| | | | |
|---|---|---|---|
| CA | 1 174 005 | 9/1984 | .......... A01N/31/14 |
| DE | 3743 821 A1 | 7/1989 | ............ B27K/3/34 |
| DE | 4217 882 A1 | 12/1993 | .......... A01N/55/04 |
| DE | 44 41 674 A1 | 5/1996 | ......... C07C/275/32 |
| DE | 196 40 874 | 4/1998 | ............ B27K/3/34 |
| DE | 196 48 888 A1 | 5/1998 | ............ B27K/3/50 |
| EP | 0 370 182 | 5/1990 | ............ B27K/3/50 |
| EP | 0 381 482 | 8/1990 | ............ B27K/3/50 |
| EP | 0 571 846 A1 | 12/1993 | .......... A01N/47/12 |
| JP | 57022003 | 2/1982 | ............ B27K/3/52 |
| JP | 64-1796 | 1/1989 | ............ C11D/3/28 |
| JP | 1-268605 | 10/1989 | .......... A01N/33/24 |
| JP | 9059672 | 3/1997 | |
| WO | 97/01423 | 1/1997 | ............ B27K/3/50 |
| WO | 98/00008 | 1/1998 | .......... A01N/25/02 |
| WO | 98/18321 | 5/1998 | .......... A01N/25/30 |
| WO | 98/31518 | 7/1998 | ............ B27K/3/00 |

OTHER PUBLICATIONS

American Wood Preservers' Association, P5–Waterborne Preservatives, 4–5, 1998.
Encyclopedia of Chemical Technology, vol. 2, pp. 259–271, John Wiley & Sons Inc., 1978.
Archer et al., Forest Products Journal, 45(1):86–89, Jan. 1995.
Hirobumi et al., 120:301698 1993 (abstract).
Liu et al., 25$^{th}$ Annual Meeting of the International Research Group on Wood Preservation, Nusa Dua Bali, Indonesia, May 29, 1994–Jun. 3, 1994.
Nicholas et al., 28$^{th}$ Annual Meeting of the International Research Group on Wood Preservation, Whistler, Canada, May 25, 1997–May 30, 1997.
Williams et al., American Wood–Perservers' Association, 90:156–176, 1994.

* cited by examiner

*Primary Examiner*—Alton Pryor
(74) *Attorney, Agent, or Firm*—Darby & Darby

(57) ABSTRACT

The present invention provides a wood preservative composition comprising an amine oxide and an isothiazolone. Another embodiment of the present invention is a method for preserving and/or waterproofing wood substrate by contacting the composition with the wood substrate.

38 Claims, No Drawings

ISOTHIAZOLONE/AMINE OXIDE WOOD PRESERVATIVES

This application claims the benefit of U.S. Serial No. 60/135,561, filed May 24, 1999.

FIELD OF THE INVENTION

This invention relates to wood preservative and waterproofing compositions containing an amine oxide and an isothiazolone.

BACKGROUND OF THE INVENTION

Isothiazolones are known to be effective as wood preservatives. Many isothiazolones, however, have low water solubility. As a result, solutions containing them often have two or more phases.

U.S. Pat. No. 5,536,305 provides compositions comprising (a) a water insoluble wood preservative compound, such as an isothiazolone; (b) a surfactant system consisting of one or more surfactants selected front the group consisting of sulfonated anionics, sulfonated anionics, sulfosuccinated anionics, quaternary ammonium cationics, and amphoterics; and (c) optionally non-polar organic solvents.

There is a continuing need for improved isothiazolone wood preservatives and waterproofing compositions which have only one phase.

SUMMARY OF THE INVENTION

Applicants have discovered that amine oxides enhance the performance of isothiazolones as wood preservatives and provide waterproofing properties. Amine oxides also aide in solubilizing isothiazolones into aqueous solutions. The present invention provides a composition comprising an amine oxide and an isothiazolone.

Another embodiment of the present invention is a method for preserving and/or waterproofing a wood substrate by contacting the wood substrate with the composition.

Yet another embodiment is an article comprising a wood substrate and the composition of the present invention.

DETAILED DESCRIPTION OF THE INVENTION

The present invention provides a composition comprising an amine oxide and an isothiazolone. The amine oxide enhances penetration of the isothiazolone into wood substrates and improves leach resistance. Furthermore, the amine oxides aide in solubilizing the isothiazolone in water. As a result, aqueous solutions containing isothiazolones and amine oxides may be formed which have only one phase. The compositions of the present invention also have low volatility.

The amine oxide may be a trialkylamine oxide; an N-alkylcyclicamine oxide; a dialkylpiperazine di-N-oxide; an alkyldi(poly(oxyalkylene))amine oxide; a dialkylbenzylamine oxide; a fatty acylamidopropyldimethylamine oxide; a diamine oxide; a triamine oxide; and any combination of any of the foregoing. Preferably, the amine oxide includes at least one $C_8$–$C_{18}$ alkyl moiety.

Preferred trialkylamine oxides have the formula $R^1R^2R^3N\rightarrow O$, where $R^1$ is a linear, branched, cyclic or any combination thereof $C_8$ to $C_{40}$ saturated or unsaturated group; and $R^2$ and $R^3$ independently are linear, branched, or any combination thereof $C_1$ to $C_{40}$ saturated or unsaturated groups. $R^1$, $R^2$, and $R^3$ independently may be alkyl, alkenyl, or alkynyl groups. More preferably, $R^1$ is a linear, branched, cyclic or any combination thereof $C_8$ to $C_{22}$ saturated or unsaturated group, such as coco, hydrogenated tallow, soya, decyl, and hexadecyl; and $R^2$ and $R^3$ independently are linear, branched, or any combination thereof $C_1$ to $C_{22}$ saturated or unsaturated groups, such as coco, hydrogenated tallow, soya, decyl, and hexadecyl.

A preferred trialkylamine oxide is a dialkylmethylamine oxide having the formula $R^1R^2CH_3N\rightarrow O$, where $R^1$ and $R^2$ are defined as above. Another preferred trialkylamine oxide is an alkyldimethylamine oxide having the formula $R^1(CH_3)_2N\rightarrow O$, where $R^1$ is defined as above. More preferred alkyldimethylamine oxides have the formula $R^{19}(CH_3)_2N\rightarrow O$, where $R^{19}$ is a linear or branched $C_8$–$C_{18}$ alkyl or alkenyl. Preferably, $R^{19}$ is a linear or branched $C_8$–$C_{16}$ alkyl. Alkyldimetlylamine oxides are non-toxic and non-mutagenic surfactants. Suitable alkyldimethylamine oxides include, but are not limited to, a $C_{10}$ alkyldimethylamine oxide, a $C_{10}$–$C_{14}$ alkyldimethylamine oxide, a $C_{12}$–$C_{16}$ alkyldimethylamine oxide, a $C_{16}$–$C_{18}$ alkyldimethylamine oxide, and any combination of any of the foregoing.

Preferred N-alkylcyclicamines oxide have the formula $R^4R^5R^6N\rightarrow O$ where $R^4$ is defined as $R^1$ above and $R^5$ and $R^6$ are linked to form a cyclic group. The cyclic group typically contains from about 4 to about 10 carbon atoms and may optionally contain oxygen, sulfur, nitrogen, or any combination of any of the foregoing. More preferred alkylcyclicamine oxides include, but are not limited to, an alkylmorpholine N-oxide, a dialkylpiperazine di-N-oxide, and any combination of any of the foregoing.

Preferred alkylmorpholine N-oxides have the formula

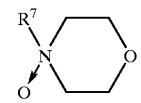

where $R^7$ is defined as $R^1$ above.

Preferred dialkylpiperazine di-N-oxides have the formula

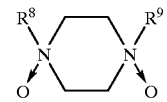

where $R^8$ is defined as $R^1$ above and $R^9$ is defined as $R^2$ above.

Preferred alkyldi(poly(oxyalkylene))amine oxides have the formula

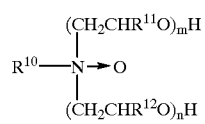

where $R^{10}$ is defined as $R^1$ above; $R^{11}$ and $R^{12}$ independently are H or $CH_3$; and m and n independently are integers from about 1 to about 10.

Preferred dialkylbenzylamine oxides have the formula $R^{13}R^{14}R^{15}N\rightarrow O$, where $R^{13}$ is defined as $R^1$ above; $R^{14}$ is defined as $R^2$ above; and $R^{15}$ is benzyl. More preferred dialkylbenzylamine oxides include, but are not limited to, alkylbenzylmethylamine oxides having the formula $R^{13}R^{15}CH_3N\rightarrow O$ where $R^{13}$ and $R^{15}$ are defined as above.

Preferred fatty acylamidopropyldimethylamine oxides have the formula

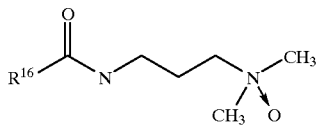

where $R^{16}$ is defined as $R^1$ above.

Preferred diamine oxides have the formula

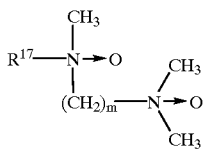

where $R^{17}$ is defined as $R^1$ above; and m is an integer from about 1 to about 10.

Preferred triamine oxides have the formula

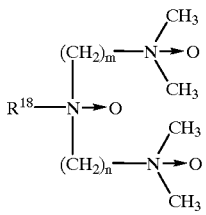

where $R^{18}$ is defined as $R^1$ above; and m and n independently are integers from about 1 to about 10.

Long chain ($C_{16}$ or greater) amine oxides, such as hexadecylamine oxides and hydrogenated tallow amine oxides, are particularly preferable for imparting waterproofing properties to the composition. Short chain ($C_{14}$ and shorter) amine oxides aide in solubilizing the isothiazolone and long chain amine oxides.

A blend of long chain and short chain amine oxides is also contemplated in one embodiment of the present invention. For example, the composition may contain a mixture of $C_{16}$–$C_{18}$ long chain amine oxides to impart waterproofing properties and $C_{10}$–$C_{14}$ short chain amine oxides to solubilize the long chain amine oxides. The long chain amine oxides may be blended with the short chain amine oxides in a ratio of about from about 1:10 to 10:1 in order to yield a stable preservative solution. More preferably, the ratio ranges from about 1:1 to about 2:1.

Suitable isothiazolones include, but are not limited to, benzisothiazolone (such as 1,2-benzisotiiazolone), 4,5-dichloro-2-octyl-3(2H)-isothiazolone, 2-octyl-3(2H)-isothiazolone, 4,5-trimethylene-3(2H)-isothiazolone, and any combination of the foregoing. Preferred isothiazolones include, but are not limited to, 3-isothiazolones, such as those disclosed in U.S. Pat. Nos. 4,105,431 and 3,761,488, both of which are wherein incorporated by reference. The composition may include a solvent, such as water and water miscible solvents, including, but not limited to, alcohols, such as ethanol; glycols; esters; ethers; polyethers; and any combination of any of the foregoing. Preferably, the composition does not include xylene and more preferably does not include a solvent other than water.

The weight ratio of amine oxide to isothiazolone broadly ranges from about 100:1 to about 1:1 and preferably from about 50:1 to 5:1.

According to one embodiment of the invention, the composition in concentrated form contains broadly from about 5 to about 100%, preferably from about 10 to about 50%, and more preferably from about 20 to about 35% by weight of combined amine oxide and isothiazolone based upon 100% weight of total composition.

Use dilutions of the composition typically comprise a biocidally effective amount of isothiazolone and a preservative enhancing and/or waterproofing effective amount of the amine oxide. Use dilutions preferably comprise from about 0.1 to about 5.0% by weight of amine oxide and from about 0.005 to about 0.5% by weight of isothiazolone based upon 100% weight of total composition.

Other adjuvants may be included in the composition as known to one of ordinary skill in the art. Other biocides, fungicides and insecticides may be include in the composition. Any organic insecticide or fungicide that can be solubilized by an aqueous amine oxide solution is suitable for use in the present composition. Suitable insecticides include, but are not limited to, chloropyrifos, folpet, captafol, captan, pyretiroids, and any combination of any of the foregoing. Suitable fungicides include, but are not limited to, iodopropargyl butylcarbamate, tributyltin oxide, 2-(thiocyanomethylthio)benzothiazole, iodo-sulfones, azoles, isothiazalones, and any combination of any of the foregoing.

Another embodiment of the present invention is a method for preserving and/or waterproofing a wood substrate by contacting the composition of the present invention with the wood substrate. The composition may be applied to the wood substrate by any method known to one of ordinary skill in the art including, but not limited to, brushing, dipping, soaking, vacuum impregnation, and pressure treatment using various cycles.

The composition of the present invention may be prepared by mixing the isothiazolone, amine oxide, solvents, and adjuvants. The mixture may be heated and/or stirred to expedite mixing.

EXAMPLES

The following examples illustrate the invention without limitation. All parts and percentages are given by weight unless otherwise indicated. All of the amine oxides in the examples are dimethylamine oxides unless otherwise indicated.

Example 1

0.9 g of a 50% (w/w) 4,5-dichloro-2-n-octyl-3-isothiazolone solution in xylene was dissolved in 30 g of a 30% (w/w) cocodimethylamine oxide (coco-DMAO) solution in water and 14.1 g of water with stirring to yield a solution containing 20% by weight of coco-DMAO and 1% by weight of 4,5-dichloro-2-n-octyl-3-isothiazolone.

Example 2

0.9 g of a 50% (w/w) 4,5-dichloro-2-n-octyl-3-isothiazolone solution xylene was dissolved in 30 g of a 30% (w/w) hexadecyldimethylamine oxide (hexadecyl-DMAO) solution in water and 14.1 g of ethanol with stirring to yield a solution containing 20% by weight of coco-DMAO and 1% by weight of 4,5-dichloro-2-n-octyl-3-isothiazolone.

Example 3

0.63 g of 72% (w/w) 1,2-benzisothiazolone in water was dissolved in 30 g of 30% (w/w) coco-DMAO in water and 14.37 g of water with stirring to yield a solution containing 20% by weight of coco-DMAO and 1% by weight of 1,2-benzisothiazolone.

Example 4

The procedure in Example 3 was performed substituting decyldimethylamine oxide (decyl-DMAO) for the coco-DMAO.

Example 5

The procedure in Example 3 was performed substituting branched alkyl($C_{10}$–$C_{14}$) dimethylamine oxide (branched alkyl ($C_{10}$–$C_{14}$)-DMAO) for the coco-DMAO. The branched alkyl ($C_{10}$–$C_{14}$)-DMAO is available as Barlox® 12i from Lonza Inc. of Fair Lawn, N.J.

Example 6

The efficacy of aqueous 1,2-benzisothiazolone/amine oxide solutions containing the amine oxides in Table 1 against the wood rot fungi *T. versicolor* (white rot fungi), *G. trabeum* (brown rot fungi), *P. placenta* (brown rot fungi), and *C. globosum* (soft rot decay fungi) were determined using the agar dilution plate method well known in the art. The water in the solution was evaporated to form an agar/biocide mixture and then tested. Each solution was tested at dilutions ranging from 10 to 5000 ppm of benzisothiazolone. The weight ratio of amine oxide to 1,2-benzisothiazolone was either 20:1 or 10:1 in each solution. The percent retardation of the fungi was determined by the percentage change in the diameter of the fungi on the agar plate (i.e. Percent Retardation=((Diameter of Control)−(Diameter of Treated Fungi))/(Diameter of Control)* 100%).

The results are shown in Table 1 below.

TABLE 1

| Amine Oxide | Concentration of Amine Oxide (ppm) | Concentration of 1,2-Benziso-thiazolone (ppm) | Percent Retardation | | | |
|---|---|---|---|---|---|---|
| | | | T. Versicolor | G. trabeum | P. placenta | C. globosum |
| Coco-DMAO | 5000 | 250 | 100 | 100 | 100 | 100 |
| | 1000 | 50 | 100 | 100 | 100 | 71 |
| | 750 | 75 | 100 | 100 | 100 | 83 |
| | 500 | 50 | 82 | 100 | 100 | 81 |
| | 500 | 25 | 100 | 100 | 100 | 74 |
| | 250 | 12.5 | 70 | 77 | 87 | 60 |
| | 100 | 10 | 52 | 79 | 87 | 40 |
| | 100 | 5 | 52 | 75 | 78 | 44 |
| | 100 | 5 | 58 | 66 | 74 | 54 |
| | 50 | 5 | 26 | 72 | 76 | 38 |
| | 25 | 2.5 | 17 | 69 | 72 | 41 |
| | 10 | 0.5 | 15 | 31 | 80 | 12 |
| Decyl-DMAO | 5000 | 250 | 100 | 100 | 100 | 100 |
| | 1000 | 50 | 100 | 100 | 100 | 100 |
| | 100 | 5 | 41 | 78 | 83 | 19 |
| | 10 | 0.5 | 11 | 23 | 53 | −13 |
| Branched alkyl ($C_{10}$—$C_{14}$) DMAO | 5000 | 250 | 100 | 100 | 100 | 100 |
| | 1000 | 50 | 100 | 100 | 100 | 100 |
| | 100 | 5 | 54 | 68 | 57 | 19 |
| | 10 | 0.5 | 14 | 9 | 17 | −13 |
| None | — | 1000 | 100 | 100 | 100 | 100 |
| | — | 500 | 100 | 100 | 100 | 83 |
| | — | 250 | 100 | 100 | 100 | 77 |
| | — | 100 | 72 | 89 | 89 | 70 |
| | — | 50 | 55 | 70 | 78 | 54 |
| | — | 25 | 50 | 79 | 86 | 44 |
| | — | 10 | 49 | 72 | 64 | 5 |
| | — | 5 | 10 | 7 | 21 | 10 |

Example 7

The efficacy of aqueous 4,5-dichloro-2-n-octyl-3-isothiazolone/amine oxide solutions containing the amine oxides in Table 2 against the wood rot fungi *T. versicolor* (white not fungi), *G. trabeum* (brown rot fungi), *P. placenta* (brown rot fungi), and *C. globosum* (soft rot decay fungi) were determined as described in Example 6.

The results are shown in Table 2 below.

TABLE 2

| Amine Oxide | Concentration of Amine Oxide (ppm) | Concentration of 4,5-dichloro-2-n-octyl-isothiazolone (ppm) | Percent Retardation | | | |
|---|---|---|---|---|---|---|
| | | | T. Versicolor | G. trabeum | P. placenta | C. globosum |
| Coco-DMAO | 5000 | 250 | 100 | 100 | 100 | 76 |
| | 1000 | 100 | 100 | 100 | 100 | 82 |
| | 1000 | 50 | 100 | 100 | 100 | 81 |
| | 1000 | 50 | 100 | 100 | 100 | 75 |
| | 750 | 75 | 100 | 100 | 100 | 74 |
| | 500 | 50 | 100 | 100 | 100 | 69 |
| | 250 | 25 | 67 | 89 | 100 | 62 |
| | 100 | 25 | 65 | 78 | 100 | 61 |
| | 50 | 12.5 | 64 | 77 | 85 | 57 |
| | 50 | 2.5 | 58 | 54 | 72 | 50 |
| Octyl-DMAO | 5000 | 250 | 100 | 100 | 100 | 100 |
| | 1000 | 50 | 100 | 100 | 100 | 84 |
| | 100 | 5 | 72 | 64 | 93 | 55 |
| | 10 | 0.5 | 15 | 3 | 26 | 43 |
| Decyl-DMAO | 5000 | 250 | 100 | 100 | 100 | 100 |
| | 1000 | 50 | 100 | 100 | 100 | 79 |
| | 100 | 5 | 18 | 67 | 65 | 63 |
| | 10 | 0.5 | 9 | 16 | 50 | 34 |
| Branched alkyl ($C_{10}$–$C_{14}$) DMAO | 5000 | 250 | 100 | 100 | 100 | 100 |
| | 1000 | 100 | 100 | 100 | 100 | 100 |
| | 1000 | 50 | 100 | 100 | 100 | 100 |
| | 750 | 75 | 100 | 100 | 100 | 100 |
| | 500 | 50 | 100 | 100 | 100 | 100 |
| | 250 | 25 | 100 | 100 | 100 | 79 |
| | 100 | 10 | 79 | 78 | 100 | 63 |
| | 100 | 5 | 50 | 64 | 56 | 63 |
| | 50 | 5 | 62 | 64 | 87 | 56 |
| | 10 | .5 | 5 | 8 | 12 | 7 |
| Hexadecyl-DMAO | 5000 | 250 | 87 | 72 | 85 | 78 |
| | 1000 | 50 | 80 | 70 | 84 | 73 |
| | 100 | 5 | 64 | 55 | 79 | 67 |
| | 10 | 0.5 | 16 | 29 | 63 | 39 |
| None | — | 750 | 100 | 100 | 100 | 100 |
| | — | 500 | 88 | 88 | 100 | 100 |
| | — | 250 | 87 | 87 | 100 | 89 |
| | — | 100 | 87 | 85 | 100 | 78 |
| | — | 50 | 82 | 83 | 100 | 67 |
| | — | 5 | 51 | 63 | 83 | 60 |
| | — | 0.5 | 12 | 11 | 42 | 63 |

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

What is claimed is:

1. A composition consisting essentially of
   (A) an amine oxide; and
   (B) an isothiazolone.

2. A composition as defined in claim 1, wherein said amine oxide is selected from the group consisting of
   (i) a trialkylamine oxide;
   (ii) an N-alkylcyclicamine oxide;
   (iii) a dialkylpiperazine di-N-oxide;
   (iv) an alkyldi(poly(oxyalkylene))amine oxide;
   (v) a dialkylbenzylamine oxide;
   (vi) a fatty acylamidopropyldimethylamine oxide;
   (vii) a diamine oxide;
   (viii) a triamine oxide; and
   (ix) any combination of any of the foregoing.

3. A composition as defined in claim 2, wherein said trialkylamine oxide has the formula $R^1R^2R^3N\rightarrow O$, wherein $R^1$ is a linear, branched, cyclic or any combination thereof $C_8$ to $C_{40}$ saturated or unsaturated group; and $R^2$ and $R^3$ independently are linear, branched, or any combination thereof $C_1$ to $C_{40}$ saturated or unsaturated groups.

4. A composition as defined in claim 3, wherein $R^1$ is a linear, branched, cyclic or any combination thereof $C_8$ to $C_{22}$ saturated or unsaturated group; and $R^2$ and $R^3$ independently are linear, branched, or any combination thereof $C_1$ to $C_{22}$ saturated or unsaturated groups.

5. A composition as defined in claim 4, wherein $R^2$ and $R^3$ independently are linear, branched, or any combination thereof $C_8$ to $C_{22}$ saturated or unsaturated groups.

6. A composition as defined in claim 3, wherein said trialkylamine oxide is a dialkylmethylamine oxide having the formula $R^1R^2CH_3N\rightarrow O$, wherein $R^1$ is a linear, branched, cyclic or any combination thereof $C_8$ to $C_{40}$ saturated or unsaturated group; and $R^2$ is a linear, branched, or any combination thereof $C_1$ to $C_{40}$ saturated or unsaturated group.

7. A composition as defined in claim 6, wherein $R^1$ is a linear, branched, cyclic or any combination thereof $C_8$ to $C_{22}$ saturated or unsaturated group; and $R^2$ is a linear, branched, or any combination thereof $C_1$ to $C_{22}$ saturated or unsaturated group.

8. A composition as defined in claim 3, wherein said trialkylamine oxide is an alkyldimethylamine oxide having the formula $R^1(CH_3)_2N{\rightarrow}O$, wherein $R^1$ is a linear, branched, cyclic or any combination thereof $C_8$ to $C_{40}$ saturated or unsaturated group.

9. A composition as defined in claim 8, wherein $R^1$ is a linear, branched, cyclic or any combination thereof $C_8$ to $C_{22}$ saturated or unsaturated group.

10. A composition as defined in claim 8, wherein said alkyldimethylamine oxide is selected from the group consisting of a $C_{10}$ alkyldimethylamine oxide, $C_{12}$–$C_{14}$ alkyldimethylamine oxide, $C_{16}$–$C_{18}$ alkyldimethylamine oxide, and any combination of any of the foregoing.

11. A composition as defined in claim 1, wherein said isothiazolone is selected from the group consisting of benzisothiazolone, 4,5-dichloro-2-octyl-3(2H)-isothiazolone, 2-octyl-3(2H)-isothiazolone, 4,5-trimethylene-3(2H)-isothiazolone, and any combination of the foregoing.

12. A composition as defined in claim 1, wherein said composition consists essentially of a biocidally effective amount of said isothiazolone.

13. A composition as defined in claim 1, wherein said composition consists essentially of a preservative enhancing and/or waterproofing effective amount of said amine oxide.

14. A composition as defined in claim 1, wherein the weight ratio of said amine oxide to said isothiazolone ranges from about 100:1 to about 1:1.

15. A composition as defined in claim 14, wherein said weight ratio ranges from about 50:1 to about 5:1.

16. A composition as defined in claim 1, wherein said composition consists essentially of from about 0.1 to about 5% by weight of said amine oxide and from about 0.005 to about 0.5% by weight of said isothiazolone based upon 100% weight of total composition.

17. A method for preserving wood, said method comprising contacting said wood with a composition as defined in claim 1.

18. A method for waterproofing wood, said method comprising contacting said wood with a composition as defined in claim 1.

19. A one phase aqueous composition consisting essentially of:
(a) one or more amine oxides; and
(b) one or more isothiazolones.

20. A composition as defined in claim 19, wherein said amine oxide is selected from the group consisting of
(i) a trialkylamine oxide;
(ii) an N-alkylcyclicamine oxide;
(iii) a dialkylpiperazine di-N-oxide;
(iv) an alkyldi(poly(oxyalkylene))amine oxide;
(v) a dialkylbenzylamine oxide;
(vi) a fatty acylamidopropyldimethylamine oxide;
(vii) a diamine oxide;
(viii) a triamine oxide; and
(ix) any combination of any of the foregoing.

21. A composition as defined in claim 20, wherein said trialkylamine oxide has the formula $R^1R^2R^3N{\rightarrow}O$, wherein $R^1$ is a linear, branched, cyclic or any combination thereof $C_8$ to $C_{40}$ saturated or unsaturated group; and $R^2$ and $R^3$ independently are linear, branched, or any combination thereof $C_1$ to $C_{40}$ saturated or unsaturated groups.

22. A composition as defined in claim 21, wherein $R^1$ is a linear, branched, cyclic or any combination thereof $C_8$ to $C_{22}$ saturated or unsaturated group; and $R^2$ and $R^3$ independently are linear, branched, or any combination thereof $C_1$ to $C_{22}$ saturated or unsaturated groups.

23. A composition as defined in claim 22, wherein $R^2$ and $R^3$ independently are linear, branched, or any combination thereof $C_8$ to $C_{22}$ saturated or unsaturated groups.

24. A composition as defined in claim 21, wherein said trialkylamine oxide is a dialkylmethylamine oxide having the formula $R^1R^2CH_3N{\rightarrow}O$, wherein $R^1$ is a linear, branched, cyclic or any combination thereof $C_8$ to $C_{40}$ saturated or unsaturated group; and $R^2$ is a linear, branched, or any combination thereof $C_1$ to $C_{40}$ saturated or unsaturated group.

25. A composition as defined in claim 24, wherein $R^1$ is a linear, branched, cyclic or any combination thereof $C_8$ to $C_{22}$ saturated or unsaturated group; and $R^2$ is a linear, branched, or any combination thereof $C_1$ to $C_{22}$ saturated or unsaturated group.

26. A composition as defined in claim 21, wherein said trialkylamine oxide is an alkyldimethylamine oxide having the formula $R^1(CH_3)_2N{\rightarrow}O$, wherein $R^1$ is a linear, branched, cyclic or any combination thereof $C_8$ to $C_{40}$ saturated or unsaturated group.

27. A composition as defined in claim 26, wherein $R^1$ is a linear, branched, cyclic or any combination thereof $C_8$ to $C_{22}$ saturated or unsaturated group.

28. A composition as defined in claim 26, wherein said alkyldimethylamine oxide is selected from the group consisting of a $C_{10}$ alkyldimethylamine oxide, $C_{12}$–$C_{14}$ alkyldimethylamine oxide, $C_{16}$–$C_{18}$ alkyldimethylamine oxide, and any combination of any of the foregoing.

29. A composition as defined in claim 19, wherein said isothiazolone is selected from the group consisting of benzisothiazolone, 4,5-dichloro-2-octyl-3(2H)-isothiazolone, 2-octyl-3(2H)-isothiazolone, 4,5-trimethylene-3(2H)-isothiazolone, and any combination of the foregoing.

30. A composition as defined in claim 19, wherein said composition consists essentially of a biocidally effective amount of said isothiazolone.

31. A composition as defined in claim 19, wherein said composition consists essentially of a preservative enhancing and/or waterproofing effective amount of said amine oxide.

32. A composition as defined in claim 19, wherein the weight ratio of said amine oxide to said isothiazolone ranges from about 100:1 to about 1:1.

33. A composition as defined in claim 32, wherein said weight ratio ranges from about 50:1 to about 5:1.

34. A composition as defined in claim 19, wherein said composition consists essentially of from about 0.1 to about 5% by weight of said amine oxide and from about 0.005 to about 0.5% by weight of said isothiazolone based upon 100% weight of total composition.

35. A method for preserving wood, said method comprising contacting said wood with a composition as defined in claim 19.

36. A method for waterproofing wood, said method comprising contacting said wood with a composition as defined in claim 19.

37. A composition consisting essentially of
(A) an amine oxide;
(B) an isothiazolone; and
(C) a solvent selected from the group consisting of water, alcohols, glycols, esters, ethers, and any combination of any of the foregoing.

38. A one phase aqueous composition consisting essentially of
(A) an amine oxide;
(B) an isothiazolone; and
(C) a solvent selected from the group consisting of water, alcohols, glycols, esters, ethers, and any combination of any of the foregoing.

\* \* \* \* \*